United States Patent
He et al.

(10) Patent No.: US 9,463,463 B2
(45) Date of Patent: Oct. 11, 2016

(54) GLUCOSE TEST DEVICE

(71) Applicants: LITE-ON ELECTRONICS (GUANGZHOU) LIMITED, Guangzhou OT (CN); Lite-On Technology Corporation, Taipei (TW)

(72) Inventors: Sz-Shian He, Taipei (TW); Chia-Chun Wei, Taipei (TW); Hung-Wei Chen, Taipei (TW); Wei-Chieh Hu, Taipei (TW)

(73) Assignees: LITE-ON ELECTRONICS (GUANGZHOU) LIMITED, Guangzhou (CN); Lite-On Technology Corporation, Taipei (TW)

( * ) Notice: Subject to any disclaimer, the term of this patent is extended or adjusted under 35 U.S.C. 154(b) by 30 days.

(21) Appl. No.: 14/306,242

(22) Filed: Jun. 17, 2014

(65) Prior Publication Data

US 2015/0298130 A1    Oct. 22, 2015

(30) Foreign Application Priority Data

Apr. 16, 2014 (TW) .............................. 103113890 A (51) Int. Cl.
| | | |
|---|---|---|
| *G01N 33/00* | (2006.01) | |
| *B01L 9/00* | (2006.01) | |
| *A61B 5/15* | (2006.01) | |
| *A61B 5/157* | (2006.01) | |
| *A61B 5/151* | (2006.01) | |

(52) U.S. Cl.
CPC ............. *B01L 9/00* (2013.01); *A61B 5/1411* (2013.01); *A61B 5/157* (2013.01); *A61B 5/150022* (2013.01); *A61B 5/15151* (2013.01); *A61B 5/15163* (2013.01); *A61B 5/15176* (2013.01);
(Continued)

(58) Field of Classification Search
CPC ........ B01L 9/00; A61B 5/1411; A61B 5/157
See application file for complete search history.

(56) References Cited

U.S. PATENT DOCUMENTS

| 7,892,183 B2 * | 2/2011 | Boecker ............... A61B 5/1411 600/573 |
| 2004/0098009 A1 * | 5/2004 | Boecker ............... A61B 5/1411 606/181 |
| 2006/0052723 A1 | 3/2006 | Roe |
| 2008/0109024 A1 | 5/2008 | Berkovitch et al. |

(Continued)

FOREIGN PATENT DOCUMENTS

| EP | 2030567 | 3/2009 |
| EP | 2130493 | 12/2009 |
| WO | 2014029583 | 2/2014 |

OTHER PUBLICATIONS

"Office Action of Europe Counterpart Application", issued on Jul. 1, 2015, p. 1-p. 4, in which the listed references were cited.

*Primary Examiner* — Sam P Siefke
(74) *Attorney, Agent, or Firm* — Jianq Chyun IP Office (57) ABSTRACT

A glucose test device and its carrying unit are provided. The glucose test device includes a housing, the carrying unit, a first push rod, and a second push rod. The carrying unit is detachably assembled in the housing. The carrying unit includes a first cartridge, lancets, a second cartridge, and strips. The first cartridge has first perforated grooves, and the lancets are slidably disposed in the first perforated grooves respectively. The second cartridge is adjacent to the first cartridge, and the second cartridge has second perforated grooves. The strips are slidably disposed in the second perforated grooves respectively. The first push rod as corresponding to the first cartridge is movably disposed in the housing. The second push rod as corresponding to the second cartridge is movably disposed in the housing, wherein the first push rod is parallel to the second push rod.

14 Claims, 6 Drawing Sheets

(52) U.S. Cl.
CPC ..... *A61B 5/15184* (2013.01); *A61B 5/150267* (2013.01); *A61B 5/150328* (2013.01); *A61B 5/150358* (2013.01); *A61B 5/150412* (2013.01); *A61B 5/150503* (2013.01); *A61B 5/150572* (2013.01); *A61B 5/15113* (2013.01); *A61B 5/15115* (2013.01); *B01L 2300/0609* (2013.01)

(56) References Cited

U.S. PATENT DOCUMENTS

2011/0282173 A1* 11/2011 Fonduca .............. A61B 5/1411 600/365
2012/0330119 A1* 12/2012 Shaanan ............ A61B 5/14532 600/347

* cited by examiner

GLUCOSE TEST DEVICE

CROSS-REFERENCE TO RELATED APPLICATION

This application claims the priority benefit of Taiwan application serial no. 103113890, filed on Apr. 16, 2014. The entirety of the above-mentioned patent application is hereby incorporated by reference herein and made a part of this specification.

BACKGROUND OF THE INVENTION

1. Field of the Invention

The invention generally relates to a test device, and more particularly, to a glucose test device with a carrying unit.

2. Description of Related Art

Following the development of technology and the increased health awareness, the general public has increasingly focused on health care related issues, and thus medical equipments have continued to evolve and be upgraded to comply with manufacturing specifications of the medical equipments and to meet the needs of the general public.

Taking a glucose test for an example, a variety of different types of lancing devices is derived from it, such as lancing pens, lancets or lancing burettes. The lancing device currently on the market are mostly consisted of a blood glucose meter in combination with a lancet and a strip; and therefore, during a process of using, a user must manually install the lancet and the strip, and after a blood sample and a test result are obtained, the user has to manually remove the used lancet and the used strip and reinstall a whole new lancet and a whole new strip before the next use. This way, even though the user may be prevented from health and testing concerns, such as bacterial infections or blood-borne infections, due to a repeat use of the lancet and the strip, but the installation steps of the lancet and the strip are complicated, and thereby is very inconvenient for the user to operate.

SUMMARY OF THE INVENTION

Accordingly, the invention is directed to a glucose test device and its carrying unit, which can avoid a process of repeatedly detaching lancets and strips, thereby improving a convenience of usage.

The glucose test device of the invention includes a housing, a carrying unit, a first push rod, and a second push rod. The carrying unit is detachably assembled in the housing. The carrying unit includes a first cartridge, a plurality of lancets, a second cartridge and a plurality of strips. The first cartridge has a plurality of first perforated grooves, and the lancets are slidably disposed in the first perforated grooves respectively. The second cartridge is adjacent to the first cartridge, and the second cartridge has a plurality of second perforated grooves. The strips are slidably disposed in the second perforated grooves respectively. The first push rod as corresponding to the first cartridge is movably disposed in housing. The second push rod as corresponding to the second cartridge is movably disposed in housing, wherein the first push rod is parallel to the second push rod.

The carrying unit of the invention is detachably disposed in a housing of a glucose test device. The carrying unit includes a first cartridge, a second cartridge, a plurality of strips, and a plurality of lancets. The first cartridge includes a first body, a carrier, and an elastic element. The first body has a plurality of first perforated grooves. The carrier is movably disposed in the first body. The elastic element is sleeved on a pillar portion of the carrier and abuts between the carrier and the first body. The second cartridge is assembled with the first cartridge to constitute a main cartridge body, wherein the second cartridge has a plurality of second perforated grooves. The strips are slidably disposed in the second perforated grooves respectively. The lancets are slidably disposed in the first perforated grooves respectively, and a holding portion of each of the lancets respectively leans against the carrier. When a needle portion of any one of the lancets moves out of the first body toward a firing direction, the carrier pushed by the said lancet moves toward a firing direction and compresses the elastic element, wherein an elastic restoring force of the elastic element is adapted to drive the carrier to move towards a direction opposite to the firing direction so as to recover the said lancet back into the first body.

In an embodiment of the invention, the first cartridge is pivoted in the housing along a first axis, and the second cartridge is pivoted in the housing along a second axis parallel to the first axis.

In an embodiment of the invention, the first perforated grooves surround the first axis and are equidistantly arranged on the first cartridge, and the second perforated grooves surround the second axis and are equidistantly arranged on the second cartridge. An amount of the first perforated grooves and an amount of the second perforated grooves are equal.

In an embodiment of the invention, when the first cartridge rotates in relative to the housing along the first axis to align one of the first perforated grooves with the first push rod, the first push rod moves into the said first perforated groove towards a firing direction parallel to the first axis, and a needle portion of the lancet in the said first perforated groove is pushed out of the first cartridge by the first push rod.

In an embodiment of the invention, when the second cartridge rotates in relative to the housing along the second axis to align one of the second perforated grooves with the second push rod, the second push rod moves into the said second perforated groove towards the firing direction, and the strip in the said second perforated groove is pushed out of the second cartridge by the second push rod.

In an embodiment of the invention, the first cartridge is assembled with the second cartridge to constitute a main cartridge body, and the main cartridge body is pivoted in the housing along a main axis.

In an embodiment of the invention, the first cartridge has a plurality of slots, the second cartridge has a plurality of hooks disposed corresponding to the slots, and the hooks are respectively engaged in the slots so as to fix the first cartridge and the second cartridge.

In an embodiment of the invention, the first push rod and the second push rod are respectively located at opposite corners of the main cartridge body.

In an embodiment of the invention, when the main cartridge body rotates in relative to the housing along the main axis to align one of the first perforated grooves with the first push rod and one of the second perforated grooves with the second push rod, the first push rod moves into the said first perforated groove towards a firing direction parallel to the main axis, and a needle portion of the lancet in the said first perforated groove is pushed out of the first cartridge by the first push rod. In addition, the second push rod moves into the said second perforated groove towards the firing direction, and the strip in the said second perforated groove is pushed out of the second cartridge by the second push rod, wherein a line-up order of the said first perforated groove on the first cartridge matches a line-up order of the said second perforated groove on the second cartridge.

In an embodiment of the invention, the first cartridge includes a first body, a first cover, a second cover, a carrier and an elastic element. The first perforated grooves are disposed at the first body. The first cover and the second cover are respectively disposed in two opposite sides of the first body, and the first cover and the second cover respectively have a plurality of through holes corresponding to the first perforated grooves. The carrier is movably disposed in the first body, and a holder portion of each of the lancets leans against the carrier. The elastic element is sleeved on a pillar portion of the carrier and abuts between the carrier and the first body.

In an embodiment of the invention, the first cartridge further includes a buffer layer. The buffer layer is disposed between the second cover and the first body for separating the through holes on the second cover from the first perforated grooves.

In an embodiment of the invention, the second cartridge includes a second body and two film layers. The second perforated grooves are disposed at the second body. The two film layers are respectively disposed at two opposite sides of the second body for covering the second perforated grooves.

In an embodiment of the invention, the carrying unit further includes a third cartridge and a plurality of supplementary elements. The third cartridge has a plurality of third perforated grooves. The glucose test device further includes a third push rod parallel to the first push rod, wherein the third push rod as corresponding to the third cartridge is movably disposed in the housing. The first cartridge, the second cartridge and the third cartridge are assembled with each other to constitute a main cartridge body, and the main cartridge body is pivoted in the housing along a main axis. The supplementary elements are slidably disposed in the third perforated grooves respectively.

In an embodiment of the invention, the first perforated grooves surround the main axis and are equidistantly arranged on the first cartridge, the second perforated grooves surround the main axis and are equidistantly arranged on the second cartridge, and the third perforated grooves surround the main axis and are equidistantly arranged on the third cartridge. An amount of the first perforated grooves, an amount of the second perforated grooves and an amount of the third perforated grooves are equal.

In an embodiment of the invention, a distance between the first push rod and the second push rod, a distance between the second push rod and the third push rod and a distance between the third push rod and the first push rod are equal to each other.

In an embodiment of the invention, when the main cartridge body rotates in relative to the housing along the main axis to align one of the first perforated grooves with first push rod, one of the second perforated grooves with the second push rod, and one of the third perforated grooves with the third push rod, the first push rod moves into the said first perforated groove towards a firing direction parallel to the main axis, a needle portion of the lancet in the said first perforated groove is pushed out of the first cartridge by the first push rod, the second push rod moves into the said second perforated groove towards the firing direction, the strip in the said second perforated groove is pushed out of the second cartridge by the second push rod, the third push rod moves into the said third perforated groove towards the firing direction, and the supplementary element in the said third perforated groove is pushed out of the third cartridge by the third push rod, wherein a line-up order of the said first perforated groove on the first cartridge, a line-up order of the said second perforated groove on the second cartridge and a line-up order of the said third perforated groove on the third cartridge are matched with each other.

In an embodiment of the invention, the holder portion has a protruding portion, and the protruding portion is positioned in a notch of the carrier, so that each of the lancets abuts against the carrier respectively.

In view of above, the carrying unit of the invention at least includes the first cartridge and the second cartridge, wherein the first cartridge is configured with a plurality of lancets therein, and the second cartridge is configured with a plurality of strips corresponding to the amount of the lancets. Therefore, each time when performing a glucose test, the glucose test device may automatically be replaced with un-used lancet and strip to perform sampling and testing of blood through using the carrying unit, and thus can avoid a process of repeatedly detaching the lancets and the strips, thereby improving a convenience of usage.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
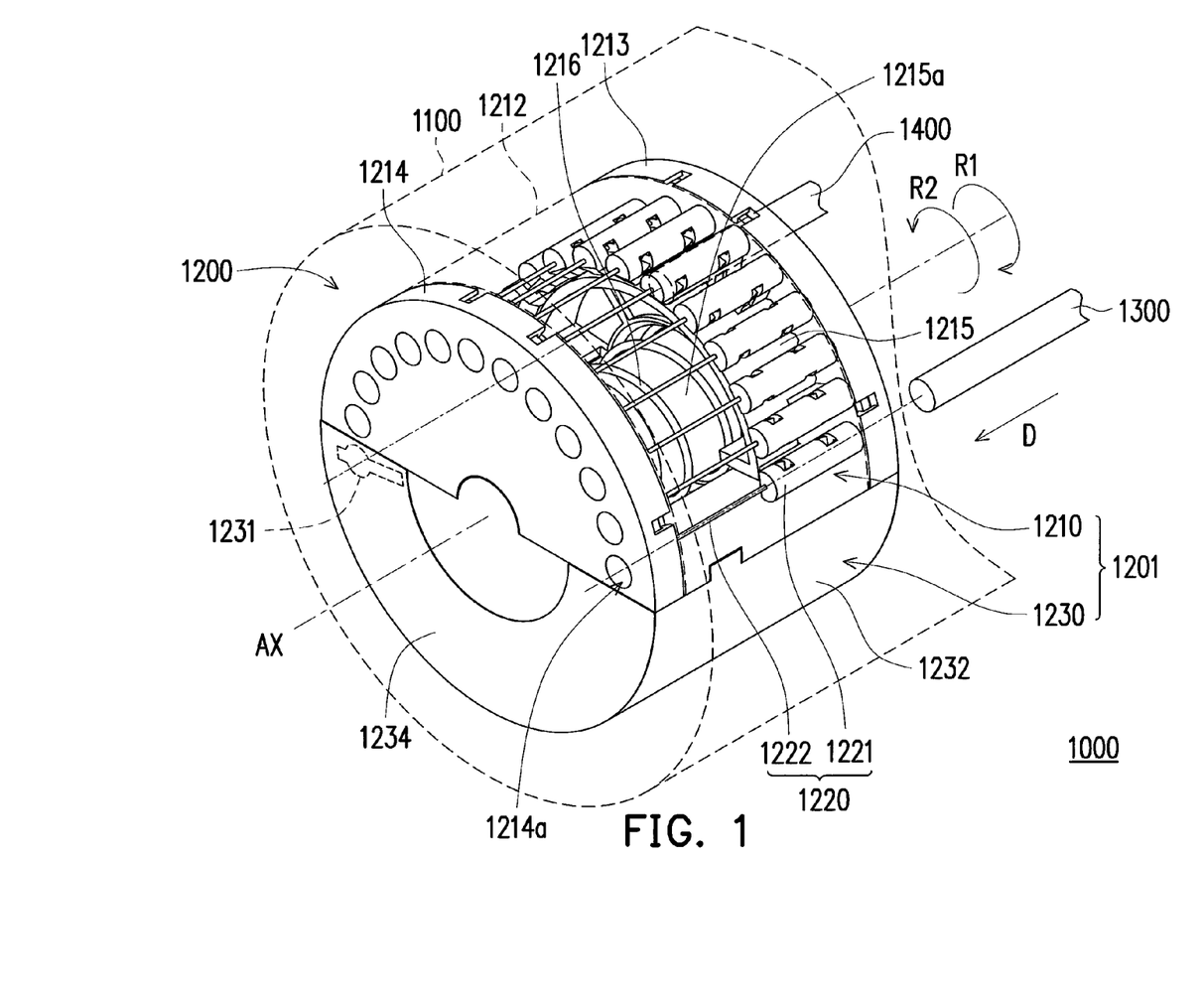
FIG. 1 is a partial schematic view illustrating a glucose test device according to an embodiment of the invention.
Figure 2:
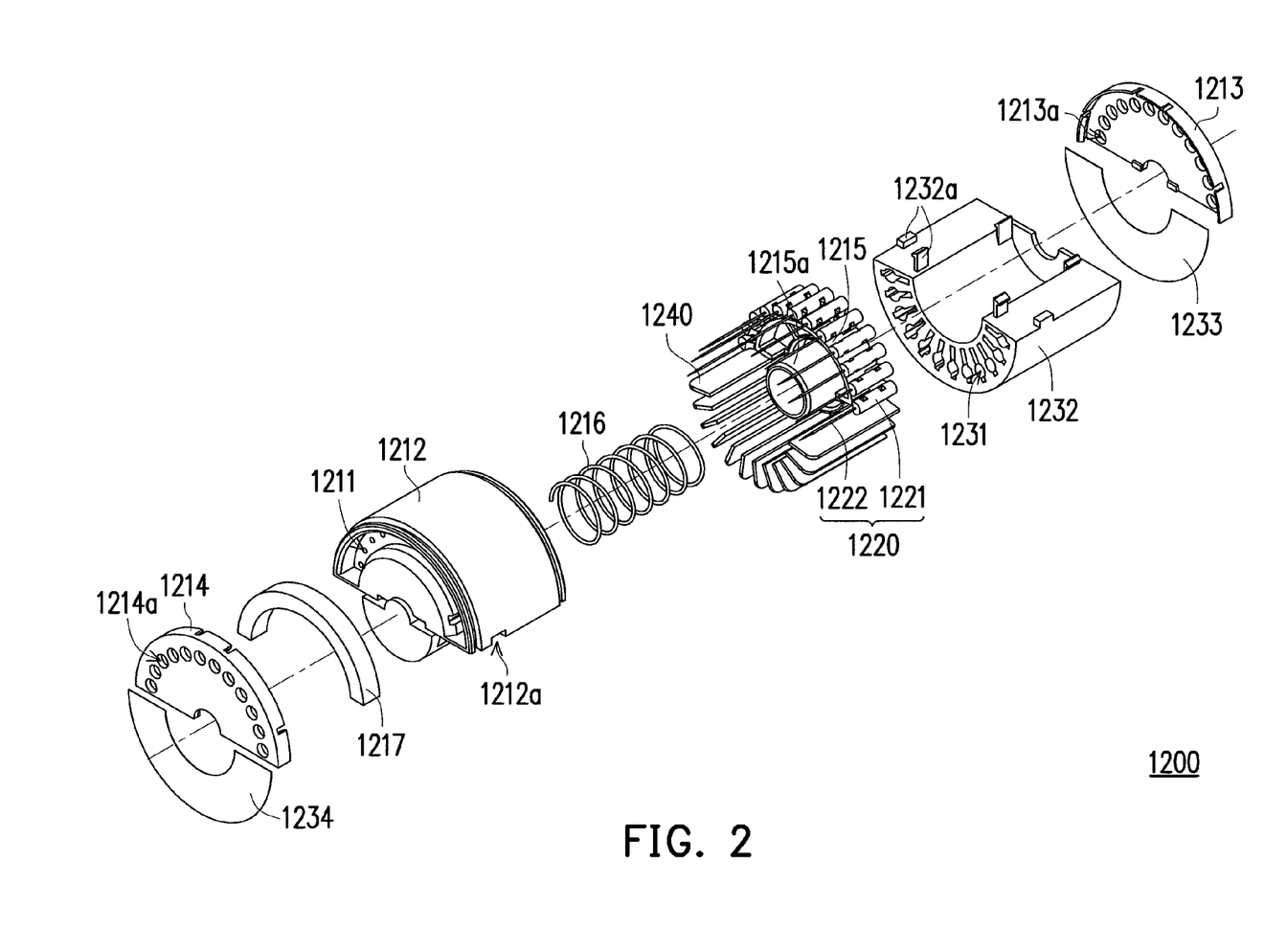
FIG. 2 is an exploded schematic view illustrating a carrying unit of FIG. 1.
Figure 3:
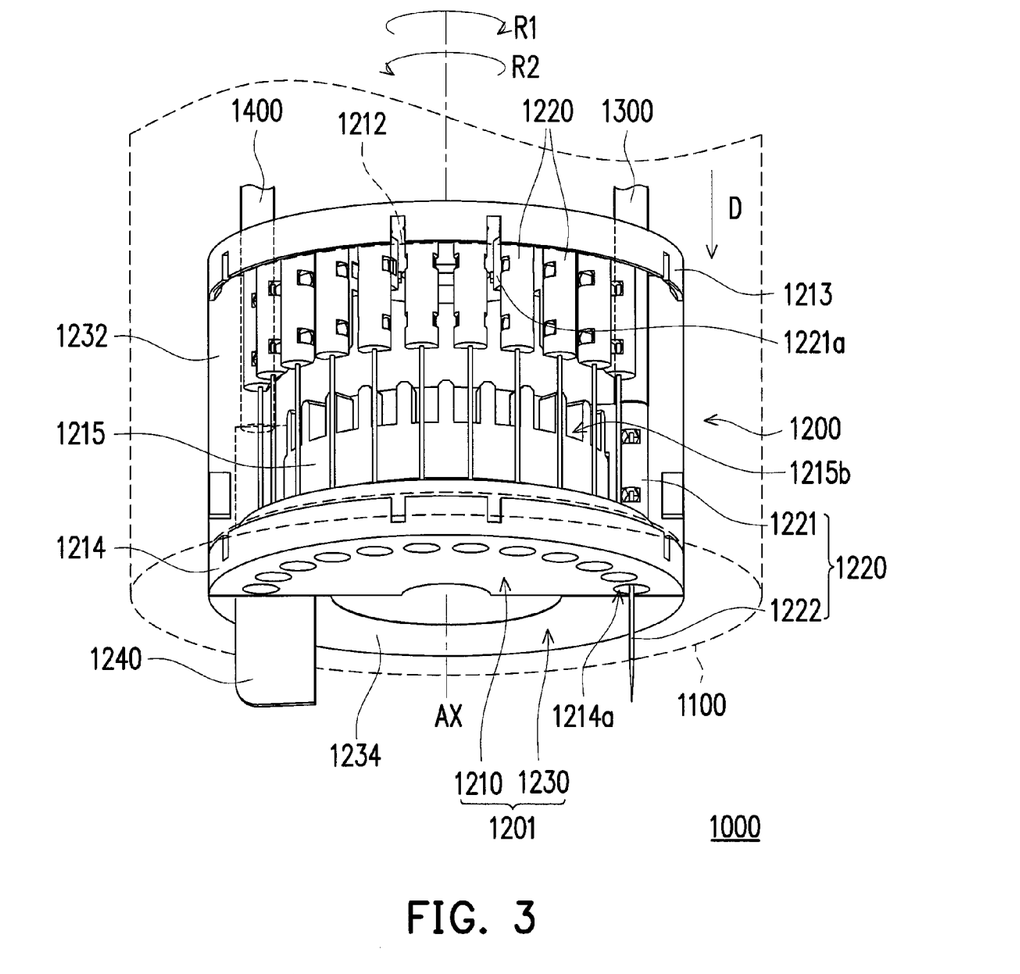
FIG. 3 is a schematic view illustrating the glucose test device of FIG. 1 pushing a lancet and a strip out of the carrying unit.

FIG. 1 is a partial schematic view illustrating a glucose test device according to an embodiment of the invention. FIG. 2 is an exploded schematic view illustrating a carrying unit of FIG. 1. FIG. 3 is a schematic view illustrating the glucose test device of FIG. 1 pushing a lancet and a strip out of the carrying unit, wherein for the description clarity, housing 1100 and first body 1212 are illustrated with dashed lines. Referring to FIG. 1 and FIG. 2, in the present embodiment, a glucose test device 1000 includes a housing 1100, a carrying unit 1200, a first push rod 1300, and a second push rod 1400, wherein the housing 1100 may be fabricated with plastic, acrylic, metal, carbon fiber, composite material or other suitable material.

The carrying unit 1200 is detachably assembled in the housing 1100 and includes a first cartridge 1210, a plurality of lancets 1220, a second cartridge 1230 and a plurality of strips 1240. The first cartridge 1210 has a plurality of first perforated grooves 1211, and the lancets 1220 are slidably disposed in the first perforated grooves 1211 respectively. The second cartridge 1230 is adjacent to the first cartridge 1210, wherein the second cartridge 1230 has a plurality of second perforated grooves 1231, and the strips 1240 are slidably disposed in the second perforated grooves 1231 respectively. Herein, the first cartridge 1210 and the second cartridge 1230 are substantially appeared to be semicylindrical in shapes and are adapted to assemble with each other to constitute a main cartridge body 1201. The main cartridge body 1201 constituted by assembling the first cartridge 1210 and the second cartridge 1230 is substantially appeared to be cylindrical in shape and is pivoted in the housing 1100 along a main axis AX.

On the other hand, an amount of the second perforated grooves 1231 and an amount of the first perforated grooves 1211 are equal, wherein the first perforated grooves 1211 surround the main axis AX and are equidistantly arranged on the first cartridge 1210, and the second perforated grooves 1231 surround the main axis AX and are equidistantly arranged on the second cartridge 1230. In the present embodiment, the first perforated grooves 1211, for example, are radially arranged on the main cartridge body 1201 along a counter-clockwise direction R2, and the second perforated grooves 1231, for example, are lined-up after the first perforated groove 1211 with a line-up order being the last, and are radially arranged on the main cartridge body 1201 along the counter-clockwise direction R2 until the second perforated groove 1231 with a line-up order being the last is adjacent to the first perforated groove 1211 with a line-up order being the first. In view of the above design principles, in an embodiment (not shown), the first perforated grooves 1211 and the second perforated grooves 1231 may also be radially arranged on the main cartridge body 1201 along a clockwise direction R1, and the invention is not limited thereto.

In the present embodiment, the first push rod 1300 as corresponding to the first cartridge 1210 is movably disposed in the housing 1100, and second push rod 1400 as corresponding to the second cartridge 1230 is movably disposed in the housing 1100, wherein the first push rod 1300 and the second push rod 1400 are parallel to each other and respectively located at opposite corners of the main cartridge body 1201. Specifically, a cross-sectional profile of the first push rod 1300 is identical to a cross-sectional profile of each of the first perforated grooves 1211, and a cross-sectional profile of the second push rod 1400 is identical to a portion of the cross-sectional profile of each of the second perforated grooves 1231. Therefore, in a subsequent process where the first push rod 1300 pushes any one of the lancets 1220 from its corresponding first perforated groove 1211 to the outside of the first cartridge 1210, the first push rod 1300 may smoothly move into the said first perforated groove 1211 to push out the said lancet 1220. And, in a subsequent process where the second push rod 1400 pushes any one of the strips 1240 from its corresponding second perforated groove 1231 to the outside of the second cartridge 1230, second push rod 1400 may smoothly move into the said second perforated groove 1231 to push out the said strip 1240.

On the other hand, the first cartridge 1210 may include a first body 1212, a first cover 1213, a second cover 1214, a carrier 1215, and an elastic element 1216. The second cartridge 1230 includes a second body 1232 and two film layers 1233 and 1234. The first body 1212 has a plurality of slots 1212a, and the second body 1232 has a plurality of hooks 1232a disposed corresponding to the slots 1212a. Therefore, in a processing of assembling the first cartridge 1210 with the second cartridge 1230, the first body 1212 may be fixed to the second body 1232 by engaging the hooks 1232a into the slots 1212a.

Specifically, the first perforated grooves 1211 are disposed at the first body 1212, and the second perforated grooves 1231 are disposed at the second body 1232. The first cover 1213 and the second cover 1214 are respectively disposed at two opposite sides of the first body 1212, and the first cover 1213 and the second cover 1214 respectively have a plurality of through holes 1213a and 1214a disposed corresponding to the first perforated grooves 1211. The film layers 1233 and 1234 are respectively disposed at two opposite sides of the second body 1232 and cover the second perforated grooves 1231, wherein the film layers 1233 and 1234 are fabricated with aluminum foil, copper foil or other suitable material, and are configured to prevent the strips 1240 from easily falling out of the second cartridge 1230 from the second perforated grooves 1231. In addition, the carrier 1215 is movably disposed in the first body 1212, wherein the elastic element 1216, for example, is sleeved on a pillar portion 1215a of the carrier 1215 and abuts between the carrier 1215 and the first body 1212. Besides, a holder portion 1221 of each of the lancets 1220 leans against the carrier 1215, and a needle portion 1222 connected to the holder portion 1221 is located in the corresponding first perforated groove 1211. More specifically, the holder portion 1221 of each of the lancets 1220 has a protruding portion 1221a, and each protruding portion 1221a may respectively be positioned in a plurality of notches 1215b of the carrier 1215, so that each of the lancets 1220 may respectively be abutting against the carrier 1215.

Referring to FIGS. 1 through 3, in the present embodiment, when the main cartridge body 1201 rotates in relative to the housing 1100 along the main axis AX (e.g., rotates along the clockwise direction R1) to align any one of the first perforated grooves 1211 with the first push rod 1300 and any one of the second perforated grooves 1231 with the second push rod 1400, the first push rod 1300 may move into the said first perforated groove 1211 towards a firing direction D parallel to the main axis AX, and the holder portion 1221 of the lancet 1220 in the said first perforated groove 1211 is pushed by the first push rod 1300, thereby causing the needle portion 1222 of the lancet 1220 to move out of the first cartridge 1210. Since the holder portion 1221 of each of the lancets 1220 is leaned against the carrier 1215, in the above mentioned process where the first push rod 1300 pushes the needle portion 1222 of the said lancet 1220 out of the first cartridge 1210, the holder portion 1221 of the said lancet 1220 may push the carrier 1215 to move towards the firing direction D by using structural interferences with the carrier 1215, so that the elastic element 1216 is compressed. Now, the holder portions 1221 of the rest of the lancets 1220 not being pushed by the first push rod 1300 are separated from the carrier 1215 and are maintained at their original positions in the first body 1212.

The first push rod 1300, before moving into one of the first perforated grooves 1211 towards the firing direction D, must firstly pass through a through hole 1213a corresponded to the said first perforated groove 1211, wherein the first push rod 1300 matches an opening profile of the through holes 1213a, so that the first push rod 1300 may smoothly pass through the through hole 1213a and move into the said first perforated groove 1211, and thereby pushes the lancet 1220 in the said first perforated groove 1211, so that the needle portion 1222 of the lancet 1220 passes through the corresponding through hole 1214a and moves out of the first cartridge 1210. Specifically, the first cartridge 1210 further includes a buffer layer 1217, wherein the buffer layer 1217 is disposed between the second cover 1214 and the first body 1212 for separating the through holes 1214a on the second cover 1214 from the first perforated grooves 1211. Therefore, when the lancet 1220 is pushed by the first push rod 1300 to move towards the firing direction D, the needle portion 1222 of the lancet 1220 may firstly pass through the buffer layer 1217 and then pass through the corresponding through hole 1214a so as to sample a user's blood.

In general, a blood sample is usually obtained by using the needle portion 1222 to puncture finger pulp of the user. Under the condition that the holder portions 1221 of other lancets 1220 are separated from the carrier 1215, the needle portions 1222 of the other lancets 1220 may be blocked by the buffer layer 1217, and thereby would not easily move out of the first cartridge 1210 from each of the corresponding through holes 1214a. For example, the buffer layer 1217 may be a sponge containing alcohol or other disinfection substances, and thus a purpose of sterilizing the needle portion 1222 of the lancet 1220 may be achieved while the needle portion 1222 passes through the buffer layer 1217, thereby lowering the chances of having bacterial infection when the user uses the needle portion 1222 to sample the blood.

On the other hand, the second push rod 1400 may move into one of the second perforated grooves 1231 towards the firing direction D, and the strip 1240 in the said second perforated groove 1231 is pushed out of the second cartridge 1230 by the second push rod 1400. Specifically, the second push rod 1400 must firstly pass through the film layer 1233 before move into the said second perforated groove 1231, so as to push the strip 1240 in the said second perforated groove 1231 towards the firing direction D. The strip 1240 as being pushed by the second push rod 1400 perforates the film layer 1234 in order to move out of the second cartridge 1230. Now, the blood sample obtained through using the lancet 1220 may drop on the strip 1240, and the strip 1240 containing the user's blood may further be tested for the user's glucose level through using a test element (not shown) in the glucose test device 1000, so as to achieve the purpose of timely monitoring the glucose level. In the above descriptions, the line-up order of the said first perforated groove 1211 on the first cartridge 1210 matches the line-up order of the said second perforated groove 1231 on the second cartridge 1230; and for the purpose of description herein, the line-up orders are, for example, the first of the first perforated grooves 1211 and the first of the second perforated grooves 1231, respectively.

After sampling of the blood, an elastic restoring force of the elastic element 1216 may drive the carrier 1215 to move towards a direction opposite to the firing direction D so as to return back to an initial position as shown in FIG. 1. At the same time, by using structure interferences between the carrier 1215 and the holder portion 1221 of the lancet 1220, when the carrier 1215 is driven by the elastic restoring force of the elastic element 1216 to move towards the direction opposite to the firing direction D, the lancet 1220 may be recover back into the first cartridge 1210, thereby preventing the used lancet 1220 from random disposal and causing environmental health distress. Now, the carrier 1215 as being returned back to the initial position may abut against the holder portion 1221 of each of the lancets 1220 so as to facilitate the subsequent use. On the other hand, the strip 1240 that containing the user's blood may be pulled back into the second cartridge 1230 by the second push rod 1400, or be recovered to a recovery tank (not shown) in the housing 1100, so as to prevent the used strip 1240 from random disposal and causing environmental health distress.

Since the carrying unit 1200 merely uses a single elastic element 1216 to recover the lancets 1220, which are being pushed out at different locations, back into the first body 1212, such that several lancets 1220 are sharing the same elastic element 1216, it does not require to individually install each of the lancets 1220 with an elastic element for recovering the lancet 1220 back into the first body 1212, thereby providing better competitiveness in the overall structure design and the cost consideration.

In view of the above, when the user is to perform the glucose level test again, the user may enable the main cartridge body 1201 to rotate in relative to the housing 1100 along the main axis AX (i.e., rotate towards the clockwise direction R1) to align the first push rod 1300 with the next first perforated groove 1211 in line and align the second push rod 1400 with the next second perforated grooves 1231 in line; namely, the first perforated groove 1211 with a line-up order being the second, and the second perforated groove 1231 with a line-up order being the second. The first push rod 1300 may move into the first perforated groove 1211 with a line-up order being the second towards the firing direction D so as to push the needle portion 1222 of the lancet 1220 out of the first cartridge 1210, and the second push rod 1400 may move into the second perforated groove 1231 with a line-up order being the second towards the firing direction D to push the strip 1240 out of the second cartridge 1230, so as to perform the blood sampling action, wherein the specific operational means of each components may be referred back to the descriptions provided in the above, and will not be repeated herein.

In the aforementioned embodiment, since the first perforated grooves 1211 and the second perforated grooves 1231 are, for example, radially arranged on the main cartridge body 1201 along the counter-clockwise direction R2, the main cartridge body 1201 has to rotate in relative to the housing 1100 along the clockwise direction R1 so as to achieve the purpose of automatically replacing the lancets 1220 and the strips 1240. In an embodiment (not shown), when the first perforated grooves 1211 and the second perforated grooves 1231 are, for example, radially arranged on the main cartridge body 1201 along the clockwise direction R1, the main cartridge body 1201 thus has to rotate in relative to the housing 1100 along the counter-clockwise direction R2 so as to achieve the purpose of replacing the lancets 1220 and the strips 1240.

In addition, since the carrying unit 1200 is detachably disposed in the housing 1100 of the glucose test device 1000, when the lancets 1220 in the first cartridge 1210 and the strips 1240 in the second cartridge 1230 are all being used, the user may detach the old carrying unit 1200 and replace a whole new carrying unit 1200 into the housing 1100 of the glucose test device 1000 for continue usage.

Figure 4:
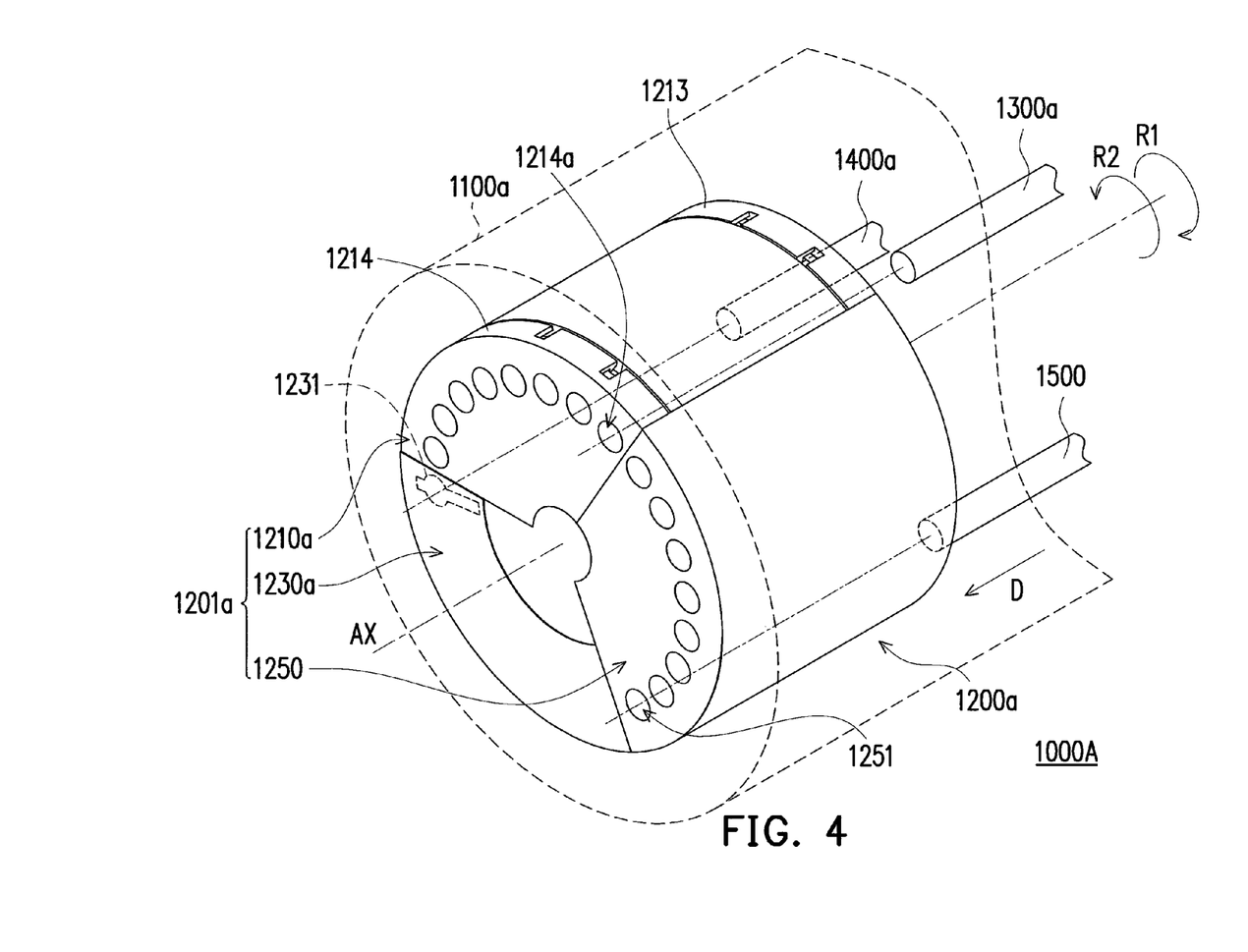
FIG. 4 is a partial schematic view illustrating a glucose test device according to another embodiment of the invention.
Figure 5:
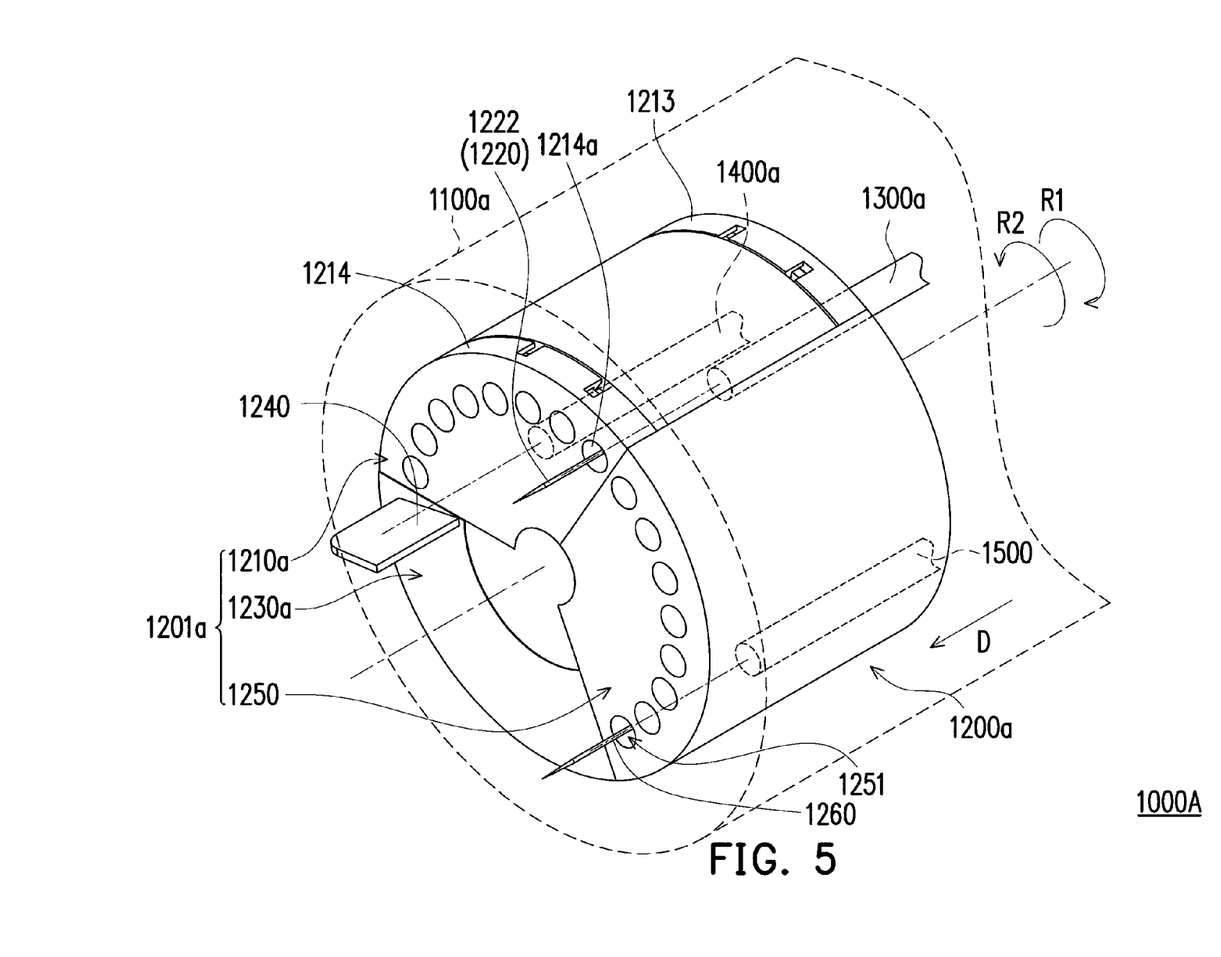
FIG. 5 is a schematic view illustrating the glucose test device of FIG. 4 pushing a lancet and a strip out of a carrying unit.

FIG. 4 is a partial schematic view illustrating a glucose test device according to another embodiment of the invention. FIG. 5 is a schematic view illustrating the glucose test device of FIG. 4 pushing a lancet and a strip out of a carrying unit. Referring to FIG. 4 and FIG. 5, different from the glucose test device 1000 of the previous embodiment, in a glucose test device 1000A of the present embodiment, a carrying unit 1200A further includes at least one third cartridge 1250 (illustrated as one in FIG. 4) and a plurality of supplementary elements 1260. The third cartridge 1250 has a plurality of third perforated grooves 1251, and the supplementary elements 1260 (e.g., insulin injection needles) are slidably disposed in the third perforated grooves 1251 respectively, wherein a first cartridge 1210a, a second cartridge 1230a and a third cartridge 1250 are assembled with each other to constitute a main cartridge body 1201a, and the main cartridge body 1201a is pivoted in the housing 1100a along the main axis AX. Component compositions in the first cartridge 1210a and the second cartridge 1230a are the same as in the first cartridge 1210 and the second cartridge 1230, and will not be repeated herein.

On the other hand, the glucose test device 1000A further includes at least one third push rod 1500 (illustrated as one in FIG. 4) parallel to the first push rod 1300a, wherein the third push rod 1500 as corresponding to the third cartridge 1250 is movably disposed in the housing 1100a. Specifically, a distance between the first push rod 1300a and the second push rod 1400a, a distance between the second push rod 1400a and the third push rod 1500 and a distance between the third push rod 1500 and the first push rod 1300a are equal to each other.

The third perforated grooves 1251 surround the main axis AX and are equidistantly arranged on the third cartridge 1250, and an amount of the first perforated grooves 1211 (not shown) in the first cartridge 1210a, an amount of the second perforated grooves 1231 (not shown) in the second cartridge 1230a and an amount of the third perforated grooves 1251 are equal. In the present embodiment, the third perforated grooves 1251, for example, are lined-up after the second perforated groove 1231 wither a line-up order being the last, and are radially arranged on the main cartridge body 1201a along the counter-clockwise direction R2 until the third perforated groove 1251 with a line-up order being the last is adjacent to the first perforated groove 1211 with a line-up order being the first. Namely, the third cartridge 1250, for example, is connected between the first cartridge 1210a and the second cartridge 1230a. In view of the above design principles, in an embodiment (not shown), the first perforated grooves 1211, the second perforated grooves 1231 and the third perforated grooves 1251 may also be radially arranged on the main cartridge body 1201a along a clockwise direction R1, and the invention is not limited thereto.

On the other hand, a cross-sectional profile of the third push rod 1500 is identical to a cross-sectional profile of each of the third perforated grooves 1251, and thus in a subsequent process where the third push rod 1500 pushes any one of the supplementary elements 1260 from its corresponding third perforated groove 1251 to the outside of the third cartridge 1250, the third push rod 1500 may smoothly move into the said third perforated groove 1251 to push out the said supplementary element 1260.

When the main cartridge body 1201a rotates in relative to the housing 1100a along the main axis AX (e.g., rotates along the clockwise direction R1) to align any one of the first perforated grooves 1211 with the first push rod 1300a, any one of the second perforated grooves 1231 with the second push rod 1400a and any one of the third perforated grooves 1251 with the third push rod 1500, the third push rod 1500 may also move into the third perforated grooves 1251 towards the firing direction D, and the supplementary element 1260 in the said third perforated groove 1251 is pushed out of the third cartridge 1250 by the third push rod 1500, wherein a line-up order of said first perforated groove 1211 on the first cartridge 1210, and a line-up order of the said second perforated groove 1231 on the second cartridge 1230 and a line-up order of the said third perforated groove 1251 on the third cartridge 1250 are matched with each other. For the purpose of description herein, the line-up orders are, for example, the first of the first perforated grooves 1211, the first of the second perforated grooves 1231 and the first of the third perforated grooves 1251. Wherein, specific operational means between the first push rod 1300a and the lancets 1220 and between the second push rod 1400a and the strips 1240 may be referred back to the above descriptions, and will not be repeated herein.

In view of the above design principles, in an embodiment (not shown), the first perforated grooves 1211, the second perforated grooves 1231 and the third perforated grooves 1251 may also be radially arranged on the main cartridge body 1201a along the clockwise direction R1, and the invention is not limited thereto. Then, the main cartridge body 1201 a has to rotate in relative to the housing 1100a along the counter-clockwise direction R2 so as to achieve the purpose of replacing the lancets 1220, the strips 1240 and the supplementary elements 1260.

In other words, the glucose test device 1000A not only can achieve the purpose of automatically replacing the lancets 1220 and the strips 1240 by using the carrying unit 1200a, but also can push the supplementary elements 1260 out of the third cartridge 1250 by using the third push rod 1500, so as to inject insulin to lower the user's glucose level when the user's glucose level being too high. On the other hand, in an embodiment (not shown), depending on the actual needs, the glucose test device 1000A may be configured with more than two third cartridges 1250, and other needles, strips or medicines in need may also be installed in the corresponding third perforated grooves 1251 so as to fulfil the user's choices, and thereby enhances a flexibility of application.

Figure 6:
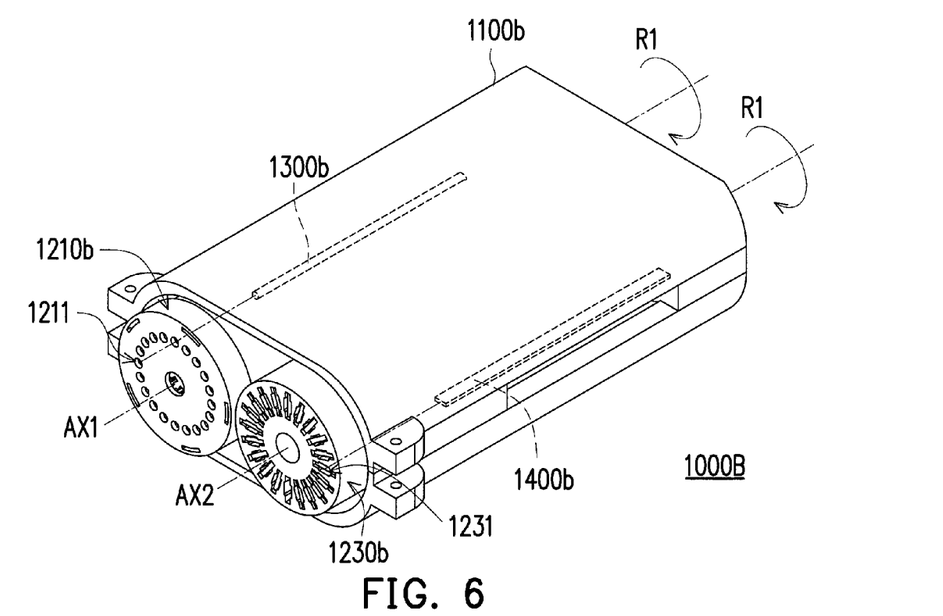
FIG. 6 is a partial schematic view illustrating a glucose test device according to yet another embodiment of the invention.
Figure 7:
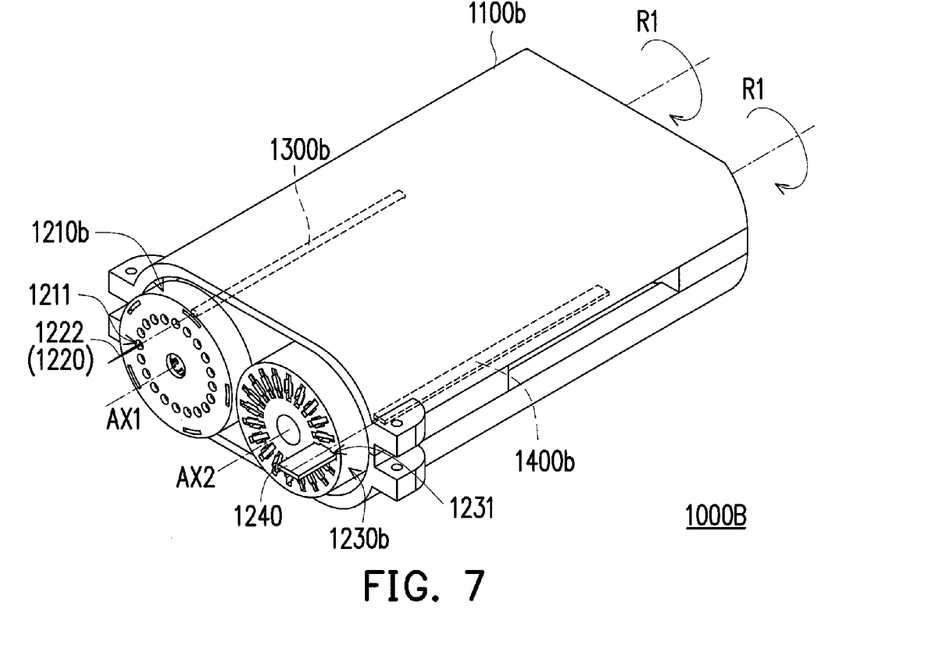
FIG. 7 is a schematic view illustrating the glucose test device of FIG. 6 pushing a lancet and a strip out of a carrying unit.

FIG. 6 is a partial schematic view illustrating a glucose test device according to yet another embodiment of the invention. FIG. 7 is a schematic view illustrating the glucose test device of FIG. 6 pushing a lancet and a strip out of a carrying unit. Referring to FIG. 6 and FIG. 7, different from the glucose test device 1000 of the previous embodiment, in a glucose test device 1000B of the present embodiment, a carrying unit 1200b includes a first cartridge 1210b and a second cartridge 1230b disposed parallel to each other, wherein the first cartridge 1210b is pivoted in the housing 1100b along a first axis AX1, and the second cartridge 1230b is pivoted in the housing 1100b along a second axis AX2 parallel to the first axis AX1.

On the other hand, the first perforated grooves 1211 surround the first axis AX1 and are equidistantly arranged on the first cartridge 1210b, the second perforated grooves 1231 surround the second axis AX2 and are equidistantly arranged on the second cartridge 1230b, and an amount of the first perforated grooves 1211 and an amount of the second perforated grooves 1231 are equal. The first push rod 1300b and the second push rod 1400b, for example, are respectively located at two opposite sides of the carrying unit 1200b. When the first cartridge 1210b rotates in relative to the housing 1100b along the first axis AX1 to align any one of the first perforated grooves 1211 with the first push rod 1300b, the first push rod 1300b moves into the said first perforated groove 1211 towards a firing direction D1 parallel to the first axis AX1, and the needle portion 1222 of the lancet 1220 in the said first perforated groove 1211 is pushed out of the first cartridge 1210b by the first push rod 1300b, so as to sample the user's blood. Herein, for the purpose of description, the first cartridge 1210b is, for example, illustrated as rotating in relative to the housing 1100*b* along the clockwise direction R1, but the invention is not limited thereto.

When the second cartridge 1230*b* rotates in relative to the housing 1100*b* along the second axis AX2 to align any one of the second perforated grooves 1231 with the second push rod 1400*b*, the second push rod 1400*b* moves into the said second perforated groove 1231 towards the firing direction D1, and the strip 1240 in the said second perforated groove 1231 is pushed out of the second cartridge 1230*b* by the second push rod 1400*b*. Then, the blood sample obtained through the lancet 1220 may drop on the strip 1240 for the subsequent testing of the user's glucose level. Herein, for the purpose of description, the second cartridge 1230*b* is, for example, illustrated as rotating in relative to the housing 1100*b* along the clockwise direction R1, but the invention is not limited thereto.

In summary, the carrying unit of the invention at least include the first cartridge and the second cartridge, wherein the first cartridge is configured with a plurality of lancets therein, and the second cartridge is configured with a plurality of strips corresponding to the amount of the lancets. In addition, the first cartridge and the second cartridge may be parallelly disposed in the housing, or may be disposed in the housing after assembled with each other to constitute the main cartridge body. Therefore, each time when performing the glucose test, the user may use the carrying unit to automatically replace lancets and strips for performing the sampling and testing of blood, and thus avoids a process of repeatedly detaching the lancets and the strips, thereby improving a convenience of usage, and further preventing the lancets and the strips from being reused and causing bacterial infection or blood-borne infection.

On the other hand, since the carrying unit is detachably disposed in the housing of the glucose test device, when the lancets in the first cartridge and the strips in the second cartridge are all being used, the user may detach the old carrying unit and replace a whole new carrying unit into the housing of the glucose test device for subsequent use. Moreover, depending on the actual needs, the glucose test device may be configured with more than two third cartridges, and other needles, strips or medicines in need may also be installed in the corresponding third perforated grooves in the third cartridge so as to fulfil the user's choices, and thereby enhances the flexibility of application.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A glucose test device, comprising:
a housing;
a carrying unit detachably assembled in the housing, the carrying unit comprising:
a first cartridge, comprising:
a first body, having a plurality of first perforated grooves;
a carrier movably disposed in the first body; and
an elastic element sleeved on a pillar portion of the carrier and abutted between the carrier and the first body;
a plurality of lancets slidably disposed in the first perforated grooves respectively, and each of the lancets leaned against the carrier respectively;
a second cartridge adjacent to the first cartridge, and the second cartridge having a plurality of second perforated grooves; and
a plurality of strips slidably disposed in the second perforated grooves respectively;
a first push rod as corresponding to the first cartridge being movably disposed in the housing; and
a second push rod as corresponding to the second cartridge being movably disposed in the housing, wherein the first push rod is parallel to the second push rod.

2. The glucose test device as recited in claim 1, wherein the first cartridge is pivoted in the housing along a first axis, and the second cartridge is pivoted in the housing along a second axis parallel to the first axis, the first perforated grooves surround the first axis and are equidistantly arranged on the first cartridge, the second perforated grooves surround the second axis and are equidistantly arranged on the second cartridge, and an amount of the first perforated grooves and an amount of the second perforated grooves are equal, wherein when the first cartridge rotates in relative to the housing along the first axis to align one of the first perforated grooves with the first push rod, the first push rod moves into the said first perforated groove towards a firing direction parallel to the first axis, and a needle portion of the lancet in the said first perforated groove is pushed out of the first cartridge by the first push rod, wherein when the second cartridge rotates in relative to the housing along the second axis to align one of the second perforated grooves with the second push rod, the second push rod moves into the said second perforated groove towards a firing direction, and the strip in the said second perforated groove is pushed out of the second cartridge by the second push rod,
and wherein a line-up order of the said first perforated groove on the first cartridge matches a line-up order of the said second perforated groove on the second cartridge.

3. The glucose test device as recited in claim 1, wherein the first cartridge is assembled with the second cartridge to constitute a main cartridge body, the main cartridge body is pivoted in the housing along a main axis, the first perforated grooves and the second perforated grooves are concentrically arranged on the main cartridge body, the first perforated grooves are located on a half of the main cartridge body, and the second perforated grooves are located on another half of the main cartridge body.

4. The glucose test device as recited in claim 3, wherein the first cartridge has a plurality of slots, the second cartridge has a plurality of hooks disposed corresponding to the slots, and the hooks are respectively engaged in the slots so as to fix the first cartridge and the second cartridge.

5. The glucose test device as recited in claim 3, wherein the first perforated grooves surround the main axis and are equidistantly arranged on the first cartridge, the second perforated grooves surround the main axis and are equidistantly arranged on the second cartridge, and an amount of the first perforated grooves and an amount of the second perforated grooves are equal.

6. The glucose test device as recited in claim 5, wherein the first push rod and the second push rod are respectively located at opposite corners of the main cartridge body.

7. The glucose test device as recited in claim 6, wherein the main cartridge body is configured to rotate in relative to the housing along the main axis to align one of the first perforated grooves with the first push rod and one of the second perforated grooves with the second push rod, the first push rod moves into the said first perforated groove towards a firing direction parallel to the main axis, a needle portion of the lancet in the said first perforated groove is pushed out of the first cartridge by the first push rod, the second push rod moves into the said second perforated groove towards the firing direction, and the strip in the said second perforated groove is pushed out of the second cartridge by the second push rod, wherein a line-up order of the said first perforated groove on the first cartridge matches a line-up order of the said second perforated groove on the second cartridge,     wherein the first perforated grooves and the second perforated grooves are radially arranged on the main cartridge body along the counter-clockwise direction, and the main cartridge body rotates in relative to the housing along the clockwise direction, or wherein the first perforated grooves and the second perforated grooves are radially arranged on the main cartridge body along the clockwise direction, and the main cartridge body rotates in relative to the housing along the counter-clockwise direction.

8. The glucose test device as recited in claim 1, wherein the first cartridge further comprises:

a first cover and a second cover respectively disposed in two opposite sides of the first body, and the first cover and the second cover respectively having a plurality of through holes corresponding to the first perforated grooves; and     a buffer layer disposed between the second cover and the first body for separating the through holes on the second cover from the first perforated grooves.

9. The glucose test device as recited in claim 1, wherein the second cartridge comprises:

a second body, the second perforated grooves disposed at the second body; and     two film layers respectively disposed at two opposite sides of the second body for covering the second perforated grooves.

10. The glucose test device as recited in claim 1, wherein the carrying unit further comprises:

a third cartridge having a plurality of third perforated grooves, the glucose test device further comprising a third push rod parallel to the first push rod, wherein the third push rod as corresponding to the third cartridge is movably disposed in the housing, the first cartridge, the second cartridge and the third cartridge are assembled with each other to constitute a main cartridge body, and the main cartridge body is pivoted in the housing along a main axis; and     a plurality of supplementary elements slidably disposed in the third perforated grooves respectively.

11. The glucose test device as recited in claim 10, wherein the first perforated grooves surround the main axis and are equidistantly arranged on the first cartridge, the second perforated grooves surround the main axis and are equidistantly arranged on the second cartridge, the third perforated grooves surround the main axis and are equidistantly arranged on the third cartridge, and an amount of the first perforated grooves, an amount of the second perforated grooves and an amount of the third perforated grooves are equal, wherein a distance between the first push rod and the second push rod, a distance between the second push rod and the third push rod and a distance between the third push rod and the first push rod are equal to each other, wherein when the main cartridge body rotates in relative to the housing along the main axis to align one of the first perforated grooves with first push rod, one of the second perforated grooves with the second push rod, and one of the third perforated grooves with the third push rod, the first push rod moves into the said first perforated groove towards a firing direction parallel to the main axis, a needle portion of the lancet in the said first perforated groove is pushed out of the first cartridge by the first push rod, the second push rod moves into the said second perforated groove towards the firing direction, the strip in the said second perforated groove is pushed out of the second cartridge by the second push rod, the third push rod moves into the said third perforated groove towards the firing direction, and the supplementary element in the said third perforated groove is pushed out of the third cartridge by the third push rod, wherein a line-up order of the said first perforated groove on the first cartridge, a line-up order of the said second perforated groove on the second cartridge and a line-up order of the said third perforated groove on the third cartridge are matched with each other.

12. The glucose test device as recited in claim 1, wherein a holder portion of each of the lancets leaned against the carrier respectively and when a needle portion of any one of the lancets moves out of the first body toward a firing direction, the carrier pushed by the said lancet moves towards the firing direction and compresses the elastic element, wherein an elastic restoring force of the elastic element is adapted to drive the carrier to move towards a direction opposite to the firing direction so as to recover the said lancet back into the first body.

13. The glucose test device as recited in claim 12, wherein the holder portion of each of the lancets has a protruding portion, and each of the protruding portions is respectively positioned in one of a plurality of notches of the carrier, so that each of the lancets abuts against the carrier respectively.

14. The glucose test device as recited in claim 3, wherein the first cartridge and the second cartridge are semicylindrical in shapes.

* * * * *